United States Patent [19]

Schwengers

[11] Patent Number: 4,673,643
[45] Date of Patent: Jun. 16, 1987

[54] PROCESS FOR THE MANUFACTURE OF ISO-MALTO-OLIGOSACCHARIDE MONOVALENT HAPTENS

[75] Inventor: Dieter Schwengers, Dormagen, Fed. Rep. of Germany

[73] Assignee: Pfeifer & Langen, Cologne, Fed. Rep. of Germany

[21] Appl. No.: 743,715

[22] Filed: Jun. 11, 1985

[30] Foreign Application Priority Data

Jun. 15, 1984 [DE] Fed. Rep. of Germany ....... 3422246

[51] Int. Cl.$^4$ ......................... C12P 19/18; C12P 19/08
[52] U.S. Cl. ........................................ 435/97; 435/103
[58] Field of Search .................................. 435/103, 97

[56] References Cited

FOREIGN PATENT DOCUMENTS 87404   8/1983   European Pat. Off. ............ 435/103

*Primary Examiner*—Lionel M. Shapiro
*Attorney, Agent, or Firm*—Sprung Horn Kramer & Woods

[57] ABSTRACT

Iso-malto-oligosaccharide monovalent haptens were prepared by adding an aqueous sucrose solution to an aqueous solution of D-glucose containing more than 300 mmol glucose per 1000 U $\alpha(1\rightarrow6)$-D-glucosyl transferase at 265 to 310 K and a pH value of from 4.5 to 8.0 and a molar ratio of sucrose to glucose of from 0.5 to 2.0. After consumption of the sucrose, glucose, liberated fructose and undesired oligosaccharides are separated in a known manner.

The process of the invention allows a particularly economical preparation of the monovalent haptens which serve for the prophylaxis of undesired dextran induced anaphylactoid side effects (DIAR).

16 Claims, No Drawings

PROCESS FOR THE MANUFACTURE OF ISO-MALTO-OLIGOSACCHARIDE MONOVALENT HAPTENS

Clinical dextran has been used for a long time in great amounts as colloidal volume substitute in the treatment of blood deficiency shock and for the thrombosis prophylaxis.

It is known that the incidence of undesired dextran-induced anaphylactoid side effects (DIAR) can be prevented by iso-malto-oligosaccharides. Iso-malto-pentaose (IM-5), iso-malto-hexaose (IM-6) and iso-malto-heptaose (IM-7) proved to be particularly effective. While iso-malto-tetraose (IM-4) is significantly less and iso-malto-tetraose (IM-3) is hardly effective, the tendency for the formation of precipitates increases with increasing chain length. Iso-malto-dodecaose (IM-12) leads in vitro again to the formation of precipitates. IM-5 to IM-7 are antigen determinants of dextran because they are strongly bonded by dextran antibodies, without resulting in the formation of precipitates. IM-5 to IM-7 accordingly act as monovalent haptens, while IM-12 is already again a bivalent antigen.

Mixtures of iso-malto-oligosaccharides which have a suitable composition as hapten for the prophylaxis of DIAR are obtained by acid hydrolysis of clinical dextran or dextran fractions of an average molecular weight of 17000 and subsequent precipitation-fractionation with ethanol. On the other hand, the clinical dextrans are prepared by partial acid hydrolysis from high molecular weight native dextran by a special control of the hydrolysis conditions and by a careful precipitation-fractionation with solvents.

The prior art methods for the preparation of monovalent haptens are, first of all, disadvantageous in that they start from partially hydrolized fractionated and, therefore, expensive dextran. About 1,000 kg sucrose are necessary to obtain 25 kilograms of the iso-malto-oligosaccharides IM-5 to IM-7 indirectly via native and clinical dextran. In addition thereto, expensive fractionating measures are necessary for obtaining the (clinical) dextrans of a specific predetermined average molecular weight.

In order to avoid the decrease of the yield of oligosaccharide mixture, based on the utilized dextran, to an economically untenable extent, glucose, iso-maltose and iso-malto-triose, which do not have any hapten effect vis-á-vis dextran antibodies, and iso-malto-oligosaccharides of a higher degree of polymerization than 11, which again as bivalent antigens already promote the formation of precipitate, are allowed to remain in the mixture during fractionation. Thus, a commercially available iso-malto-oligosaccharide mixture consists of about 20% of the ineffective components glucose, iso-maltose and iso-malto-triose and of about 10% of iso-malto-oligosaccharides of a higher degree of polymerization than 11.

Since the iso-malto-oligosaccharide mixture is prepared by acid hydrolysis of dextran which exhibits a certain degree of branching, though to a minor extent, also the oligosaccharides of the mixture are branched to a minor extent. Their proportion does not contribute anything to the hapten effect of the mixture.

Due to these disadvantages, the application of the iso-malto-oligosaccharides, prepared according to the prior art process, as pre-injection to clinical dextran for the inhibition of DIAR was not completely satisfactory.

The object of the invention is to prepare monovalent haptens for the prophylaxis of DIAR which contain as far as possible only non-branched iso-malto-oligosaccharides with a high proportion of IM-4, IM-5, IM-6 and IM-7.

This problem is solved by the process of this invention which is characterized by adding to an aqueous solution of D-glucose containing more than 300 mmol D-glucose per 1000 U $\alpha(1\rightarrow6)$-D-glucosyl transferase, at 265 to 310 K and a pH value of 4.5 to 8.0 an aqueous solution of sucrose, in such an amount that the molar ratio of sucrose to glucose is from 0.5 to 2.0, and by separating after the consumption of the sucrose the glucose liberated fructose and undesired oligosaccharides in a known manner.

The reaction mixture is preferably maintained at 290 to 300 K and a pH value in the range of 5 to 6.5. Both parameters have an influence on the structure of the resulting products.

According to the classification of the "Enzyme Commission", enzymes which transfer the D-glucopyranosyl group of sucrose to suitable acceptors are designated as $\alpha(1\rightarrow6)$-D-glucosyl transferase. An extracellular enzyme of this kind is dextran sucrase (E.C. 2.4.1.5) which is formed by specific kinds of bacteria of the lactobacilli species, for example, Leuconostoc mesenteroides, in particular the strain B-512, Leuconostoc dextranicum, streptococcus and lactobacillus. When preparing dextran, sucrose serves primarily as acceptor and acts as chain initiator for a chain polymerization in which by virtue of continuous transfer of D-glucopyranosyl groups from the sucrose to the growing chain the polysaccharide dextran having molecular masses of several millions is formed, while, at the same time, a fructose molecule is liberated for each reacted molecule of sucrose.

If one uses in this reaction other mono- di- or trisaccharides as acceptor, oligosaccharides are produced to a minor extent at the expense of the dextran. When employing glucose as acceptor, about 78 percent dextran and, as by-product, about 9 percent oligosaccharides (IM-3 to IM-12) are produced. (Robyt and Eklund, Carbohydrate Research 121 (1983) 279–286). Typically, the oligosaccharides are produced in decreasing amounts with increasing degree of polymerization.

It is possible under the reaction conditions of the present invention to control the transfer of glucosyl groups from sucrose to glucose in such a way that no dextran is produced, but the iso-malto-oligosaccharides IM-4 to IM-8 are formed in high yields. It is surprising in this connection that the iso-malto-oligosaccharides are no longer formed in decreasing amounts with increasing degree of polymerization, but that there exists a distribution maximum in the range of IM-4 to IM-6.

According to the process of this invention, it is recommendable for obtaining a high yield of the desired haptens to add the aqueous solution of sucrose continuously at such a rate that the amount of enzyme can immediately convert the amount of sucrose being fed thus avoiding an accummulation of sucrose in the reaction mixture which may lead to uncontrolled formation of high molecular weight dextran. At all events, the sucrose content in the carbohydrate dry substance of the reaction mixture should not exceed 25 percent at the equilibrium condition of the continuous reaction.

Instead of the purified dextran-sucrase, also the mixture comprising the enzyme and the bacteria which produce said enzyme may be employed.

The synthesis may be described as follows:

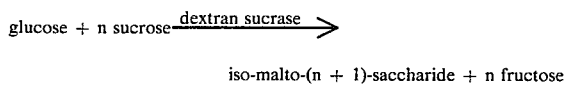

iso-malto-(n + 1)-saccharide + n fructose whereby n represents the number of moles of the utilized sucrose.

This reaction may be controlled according to the invention in such a manner that iso-malto, oligo- or polysaccharides having the desired molecular weight are obtained. Under the specified conditions of temperature and hydrogen ion concentration, the molecular weight obtained by this synthesis depends on the molar amount of the acceptor (glucose) based on a specific enzyme activity in the solution, and the molar ratio of the overall sucrose fed to the acceptor.

The enzyme activity unit U (=Unit) is the amount of enzyme which converts 1 $\mu$mol sucrose per minute at a pH of 5.2 and 298 K. If more sucrose is fed than the enzyme activity is able to convert, the control of the size of the molecules will no longer be possible. Based on the same sucrose conversion, the resulting molecular weight increases with decreasing molar ratio of glucose to enzyme activity.

If an enzyme activity of 1000 U is taken as basis, the desired oligosaccharide mixture, having an average molecular weight of from about 1000 to 1200, will be obtained at an overall sucrose addition of 1000 mmol and from 400 to 800 mmol, e.g. 600 mmol glucose.

The molar ratio of the sucrose to the provided glucose amounts to 0.5-2.0:1, preferably 0.8-1.2:1, in particular 1:1.

It is thus possible to control in a few preliminary tests with changing molar amounts of glucose within the specified ranges at predetermined activity of the $\alpha(1\rightarrow 6)$-D-glucosyl transferase (e.g. 1,000 U) and a constant amount of sucrose (e.g. 1,000 mmol) the linkage of the D-glucose pyranosyl groups of the sucrose to the glucose as acceptor in such a manner that fractions of each of the desired iso-malto-oligo-saccharides having a narrow molecular weight distribution can by synthesized in high yield.

It is possible to provide the entire necessary amount of glucose, or, while observing the other reaction conditions, in particular the concentration ratios, to continuously replace the glucose to the extent to which it is consumed as acceptor. It is also possible to conduct the synthesis reaction continuously.

An unexpected advantage of the process of the invention is that the carbohydrate content in the dry substance of the reaction mixture may be very high, in that it amounts to 30 to 50 percent, in particular 40 to 50 percent. It was surprisingly found that the formation of the disaccharide leucrose was considerably reduced, as compared to a batchwise enzymatic reaction.

A further surprising advantage of the process of the present invention resides in that the iso-malto-oligosaccharides prepared according to said process are less contaminated by branched oligosaccharides than those obtained by the acid hydrolyses of dextrans.

It was found that in the case of the continuous feed of sucrose, the proportion of iso-malto-oligosaccharides having 10 or more anhydroglucose units ($\geq$IM-10) is a suitable indicator for the formation of a high proportion of the desired monovalent haptens IM-5 to IM-7. Accordingly, it is recommandable to terminate the feed of sucrose as soon as the proportion of IM=10 has attained about 10% of the carbohydrate dry substance in the reaction mixture.

The proportion of IM-4 to IM-8 in the carbohydrate dry substance of the reaction mixture amounts to about 25%.

Although the enzymatic synthesis according to the invention is carried out under sterile conditions, as is, for example, conventional in the synthesis of native dextran, antimitotics (mytosis inhibitors) such as sulfurons acit, in amounts of up to 1.000 mg/kg, particularly 400 to 600 mg/kg, may be added to the reaction mixture in order to avoid undesired growth of yeast.

The recovery of the desired monovalent haptens from the reaction mixture by separation of the non-reacted glucose, the liberated fructose, the di- and trisaccharides and the iso-malto-oligosaccharides having a higher degree of polymerization than 11 can be effected according to prior art methods, e.g. by precipitation-fractionation with ethanol. The separation of the by-products by chromatography by means of a column filled with a strongly acid cation-exchanger has proved to be very suitable.

The process of the present invention exhibits not only the above-described advantage of the formation of unbranched iso-malto-oligosaccharides with a high proportion of IM-4 to IM-8, in particular IM-5 to IM-7, which, as monovalent haptens, are particularly suitable for preventing anaphylactoid side effects of the dextran, but it also means, as compared to the indirect way via native and clinical dextran, the reduction of the amount of sucrose to about one tenth of the amount necessary for the same amount of hapten, i.e. instead of 1000 kg sucrose, only 100 kg sucrose are necessary for 25 kg of hapten.

The reaction mixture obtained according to the process of the invention, comprising the iso-malto-oligosaccharides including the mono- and disaccharides may be directly used as low-calorie sweetening agent. After the separation of the mono- and disaccharides, the remaining iso-malto-oligosaccharide mixture may be used as almost calorie-free carrier for sweetening agents.

EXAMPLE 22 kilograms of crystalline glucose were dissolved at 298 K in 30 l of an aqueous solution of the enzyme dextran sucrase, said solution had an activity of 5,800 U/l. The pH of the solution was 5.4. 100 kg of a 40%-sucrose solution having a pH of 5.4 were continuously pumped into said solution within 24 h. 2 hours after termination of the sucrose feed, the enzyme was deactivated by heating the reaction mixture to 70° C.

The result of the saccharide mixture-analysis was:

| >IM-10 | 1.3 | | |
|--------|-----|------|------|
| IM-10  | 1.2 | IM-4 | 6.2  |
| IM-9   | 2.6 | IM-3 | 4.1  |
| IM-8   | 3.1 | IM-2 | 4.6  |
| IM-7   | 4.1 | leucrose | 4.0 |
| IM-6   | 5.3 | glucose | 25.8 |
| IM-5   | 7.4 | fructose | 30.3 |

51 liters of this saccharide solution were placed in a chromatography separating plant containing 400 l strongly acid cation exchange resin loaded with calcium ions and the individual saccharides were eluted from the column by feeding 43 l/h of distilled water.

After a preliminary run of 54 l, the main amount of iso-malto-oligosaccharides was eluted within the next 35 l from the separating column. This fraction had the following composition:

| >IM-10 | 6.6 | IM-6 | 15.9 |
|---|---|---|---|
| IM-10 | 6.1 | IM-5 | 19.9 |
| IM-9 | 7.8 | IM-4 | 13.7 |
| IM-8 | 10.6 | IM-3 | 4.9 |
| IM-7 | 13.5 | IM-2 | 1.0 |

Thus, it consisted of 63% of the desired saccharides IM-7, IM-6, IM-5 and IM-4.

The IM-5 was separated from this mixture by means of gel chromatography and its completely linear structure was conformed by nuclear magnetic resonance spectroscopy.

I claim:

1. A process for the manufacture of iso-malto-oligosaccharide monovalent haptens, comprising adding to an aqueous solution of D-glucose containing more than 300 mmol glucose per 1000 U $\alpha(1\rightarrow6)$-D-glucosyl transferase, at temperatures from 265 to 310 K and at a pH value of 4.5 to 8, an aqueous sucrose solution in such an amount that the molar ratio of sucrose to glucose is 0.5 to 2.0; and by separating, after the consumption of the sucrose glucose, liberated fructose and undesired oligosaccharides.

2. A process according to claim 1, wherein the aqueous glucose solution contains 400 to 800 mmol glucose per 1000 U enzyme.

3. A process according to claim 1, wherein the enzymatic reaction is carried out at 290 to 300 K.

4. A process according to claim 1, wherein the pH value of the reaction mixture is 5 to 6.5.

5. A process according to claim 1, wherein the molar ratio of sucrose to glucose is 0.8 to 1.2.

6. A process according to claim 1, wherein the sucrose solution is added continuously.

7. A process according to claim 1, wherein the sucrose solution is added at such a rate that the sucrose is directly converted by $\alpha(1\rightarrow6)$-D-glucosyl transferase.

8. A process according to claim 1, wherein the addition of sucrose is terminated when the content of iso-malto-oligosaccharides having at least 10 anhydroglucose units is 10% of dry weight of the carbohydrate content of the reaction mixture.

9. A process according to claim 1, wherein the dry weight of the carbohydrate content of the reaction mixture is 30 to 50 percent.

10. A process according to claim 1, wherein the $\alpha(1\rightarrow6)$-D-glucosyl transferase used is the dextran sucrase produced by the bacterium Leuconostoc mesenteroides, strain B-512.

11. A process according to claim 1, wherein the $\alpha(1\rightarrow6)$-D-glucosyl transferase used is the dextran sucrase produced by the bacterium Leuconostoc dextranicum.

12. A process according to claim 1, wherein the separation of the by-products by chromatography is carried out using a column filled with a strongly acid cation-exchanger.

13. A process according to claim 1, wherein the by-products are separated by precipitation-fractionation by means of solvents.

14. A process according to claim 1, wherein D-glucose is continuously replaced to the same extent as it is consumed as acceptor.

15. A process according to claim 1, wherein antimitotics are added in order to avoid undesired yeast growth.

16. A process according to claim 15, wherein sulfurous acid in an amount up to 1000 mg/kg is added.

* * * * *